United States Patent
Malak

(10) Patent No.: US 7,462,496 B2
(45) Date of Patent: Dec. 9, 2008

(54) PLASMON-ENHANCED MARKING OF FRAGILE MATERIALS AND OTHER APPLICATIONS THEREOF

(75) Inventor: Henryk Malak, Ellicott City, MD (US)

(73) Assignee: American Environmental System, Inc., Ellicott City, MD (US)

(*) Notice: Subject to any disclaimer, the term of this patent is extended or adjusted under 35 U.S.C. 154(b) by 141 days.

(21) Appl. No.: 11/065,612

(22) Filed: Feb. 25, 2005

(65) Prior Publication Data

US 2005/0142605 A1 Jun. 30, 2005

Related U.S. Application Data

(63) Continuation-in-part of application No. 10/930,608, filed on Sep. 1, 2004, which is a continuation-in-part of application No. 10/916,560, filed on Aug. 12, 2004, which is a continuation-in-part of application No. 10/689,965, filed on Oct. 22, 2003, now abandoned, which is a continuation-in-part of application No. 10/656,629, filed on Sep. 8, 2003, now abandoned.

(60) Provisional application No. 60/589,883, filed on Jul. 22, 2004.

(51) Int. Cl.
*G01N 33/551* (2006.01)
*G01N 33/553* (2006.01)

(52) U.S. Cl. .................. 436/524; 435/6; 436/518; 436/525; 436/172; 436/805

(58) Field of Classification Search .................. None
See application file for complete search history.

(56) References Cited

U.S. PATENT DOCUMENTS 5,527,712 A * 6/1996 Sheehy ........................ 436/525

* cited by examiner

*Primary Examiner*—Christopher L Chin

(57) ABSTRACT

The methods and applications of a surface plasmon resonance-enhanced marking technique are disclosed. The technique uses surface plasmon resonance (SPR) excited nanoparticles and a surface plasmon resonance source in nonlinear interactions with nearby chemical substances and medium for marking purposes. The SPR-enhanced absorption and fluorescence rates of chemical substances or medium and nonlinearity of SPR interactions with chemical substances or medium make the proposed method suitable for marking fragile materials including biomaterials, such as writing on thin plastic foils or DNA-protein crosslinking. The marking method can also be applied to a three-dimensional recording and read out information system with subwavelength resolutions, coding information of secrete documents, drug delivery, tissue surgery, tattoo writing or removal, photodynamic therapy, cosmetic and dermatological treatment.

13 Claims, 8 Drawing Sheets

Two-Photon Marking

PLASMON-ENHANCED MARKING OF FRAGILE MATERIALS AND OTHER APPLICATIONS THEREOF

CROSS REFERENCE TO RELATED APPLICATIONS

This application is a continuation-in-part of U.S. patent application Ser. No. 10/656,629, filed Sep. 8, 2003 now abandoned entitled "Optochemical Sensing with Multi-Band Fluorescence Enhanced by Surface Plasmon Resonance" and a continuation-in-part of U.S. patent application Ser. No. 10/689,965, filed Oct. 22, 2003, now abandoned entitled "Plasmon Enhanced Body Treatment and Bacterial Management"; and a continuation-in-part of U.S. patent application Ser. No. 10/916,560, filed Aug. 12, 2004 entitled "Methods and Devices for Plasmon Enhanced Medical and Cosmetic Procedures"; and a continuation-in-part of U.S. patent application Ser. No. 10/930,608 filed Sep. 01, 2004 entitled "Method of Plasmon-Enhanced Properties of Materials and Applications Thereof", and U.S. provisional patent Ser. No. 60/589,883, filed Jul. 22, 2004 entitled "Methods for Plasmon-Enhanced Marking of Materials and Use Thereof", each of which is incorporated by reference herein in their entirety.

STATEMENT REGARDING FEDERALLY SPONSORED RESEARCH

There is NO claim for federal support in research or development of this product.

FIELD OF THE INVENTION

The invention relates to the use of advances in nanotechnology, particularly applications of surface plasmon resonance of nanomaterials, for enhancing marking techniques.

BACKGROUND OF THE INVENTION

In spite of many inventions related to marking, current marking techniques still cannot be used in many applications. One of these applications is high efficiency, minimally invasive marking of biomaterials, like DNA and proteins, but not only limited to them. DNA absorption rates of lowest excited state (LES) and higher excited states (HES) are very small, which means that high intensity UV light is needed to excite DNA to LES and then high intensity UV-VIS-NIR light to excite DNA from LES to HES. The high intensity UV light not only excites DNA but also generates photoproducts from photolysis of water and photodamaging of other molecules. These photoproducts are very reactive chemical species which can interact with DNA, proteins, and other biomolecules causing their substantial damage and are carcinogenic to the body. The damaged biomolecules cannot be used for further biomaterial production and research. Another example of the great need for minimally invasive marking is writing on very fragile materials, like thin foils used, for example, as packaging materials. Current optical, electrical, thermal, or other marking techniques can potentially damage thin foils. Clear writing on thin foils without damaging foils is difficult to achieve, because the energy thresholds of the writing effect and the damaging foil are very similar. Therefore, exists the great need for techniques that will provide lower energy thresholds for writing, e.g. enhanced efficiency of the marking effect, and higher energy thresholds for damaging foils.

Marking with high spatial and three-dimensional resolutions is also needed, particularly in memory devices, like hard drives, CD disks, and electronic printed boards, but not limited to them. Therefore, there is a great need for marking techniques with inherent subwavelength, atomic or molecular resolutions and for techniques enabling three-dimensional writing in materials.

The invention described here fulfills the above mentioned current great needs in marking techniques and can be also used in other marking applications.

REFERENCES

The following are scientific reports found that may be associated within the herein disclosed invention.

M. Kerker, "Optics of colloid silver", *J. Colloid Interface Sci.* 105, 298 (1985)

Lakowicz et al, "Intrinsic fluorescence from DNA can be enhanced by metallic particles", *Biochem. Biophys. Res. Comm.* 286, 875 (2001)

Gryczynski et al., "Multiphoton excitation of fluorescence near metallic particles: enhanced and localized excitation", *J. Phys. Chem. B,* 106, 2191 (2002)

M. Moskovits: *Rev. Mod. Phys.* 57, 783 (1985)

T. L. Haslett, L. Tay, M. Moskovits: J. Chem. Phys. 113, 1641 (2000), and references therein K. Kneipp, Y. Wang, H. Kneipp, L. T. Perelman, I. Itzkan, R. R. Dasari, M. S. Feld: *Phys. Rev. Lett.* 78, 1667 (1997)

Ditlbacher H. et al., Electromagnetic interaction of fluorophores with designed two-dimensional silver nanoparticle arrays, *Appl. Phys. B* 73, 373-377 (2001)).

M. D. Galanin, and Z. A. Chizhikova, "Fluorescence from the second excited electronic level and absorption by excited R6G molecules", *Bull. Acad Sc., Phys. Ser.* 36, 850 (1972)

Akhilesh K. Nagaich, Dawn A. Walker, Ron Wolford, and Gordon L. Hager, Rapid Periodic Binding and Displacement of the Glucocorticoid Receptor during Chromatin Remodeling, Molecular Cell, Vol. 14, 163-174(2004)

Ch. Russmann, J. Stollhof, C. Weiss, R. Beigang and M. Beato, Two wavelength femtosecond laser induced DNA-protein crosslinking, *Nucleic Acids Research,* Vol. 26, No. 17 3967-3970 (1998)).

Jean-Marc L. Pecourt, Jorge Peon, and Bern Kohler, Ultrafast Internal Conversion of Electronically Excited RNA and DNA Nucleosides in Water, *J. Am. Chem. Soc.* 122, 9348-9349 (2000)

SUMMARY OF THE INVENTION

A method for a surface plasmon resonance-enhanced multiband absorption and multiband fluorescence marking technique and applications are described. The technique uses surface plasmon resonance (SPR) excited nanoparticles and a surface plasmon resonance source to nonlinearly excite nearby chemical substances and/or media for marking purposes. The nanoparticles are made preferably of noble metals and their sizes range from single to thousands of nanometers. The type of metal and the shape, and size of the nanoparticle is selected to match the nanoparticle SPR absorption bands with the one or both lowest (LES) and higher (HES) excited states absorption bands of the chemical substances and/or media. Under such conditions, the absorption rates of the chemical substances and/or media can be enhanced a thousand times which leads to more efficient marking. Because of the SPR nonlinear excitation of the chemical substances and/or media, the marking is much more sensitive and can be applied for marking fragile materials including biomaterials.

The method also describes a minimally invasive crosslinking of biomaterials, particularly SPR-enhanced DNA-protein crosslinking. The method also describes SPR-enhanced multiband absorption and multiband fluorescence marking performed two- and three-dimensionally in the medium with a subwavelength resolution for recording and other marking purposes.

DETAILED DESCRIPTION OF PREFERRED EMBODIMENTS

1. Abbreviations and Definitions marking—a process in which a substance or material under chemical and/or physical interactions changes its chemical-physical properties SPR—surface plasmon resonance generated in a nanoparticle under illumination by electromagnetic radiation and other forms of energy one-photon mode of excitation—process in which molecule is excited by a one photon absorption event two-photon mode of excitation—process in which a molecule is excited by simultaneous absorption of two photons multi-photon mode of excitation—process in which a molecule is excited by simultaneous absorption of three or more photons step-wise mode of excitation—process in which a molecule is excited by absorption of one photon and subsequently by absorption of second photon up-conversion mode of excitation—process in which a molecule is excited by a photon whose energy is lower than that of the lowest excited state of the molecule nanoisland—a nanoparticle on a substrate without defined shape aerogel—a nanoporous material quantum dot—a nanoparticle, whose size is a few nanometers and exhibits luminescence properties LED—light emitting diode UV light—ultraviolet light UV-VIS-NIR light—ultraviolet, visible and near-infrared light multiband absorption—absorption to a lowest excited state and to higher excited states of a molecule multiband fluorescence—fluorescence from a lowest excited state and from higher excited states of a molecule single band absorption—absorption to any excited state of a molecule single band fluorescence—fluorescence from any excited state of a molecule LES—a lowest excited state of a molecule HES—higher excited states of a molecule optically nonlinear medium—medium in which absorption of light by medium is nonlinearly dependent on intensity of light transient absorption—absorption from the lower excited state to higher excited states of a molecule recognitive material substance—a material where the external surface is covered with recognitive chemical ligands, immunolabels, phage display or other type recognitive substances 4-Pi illumination technique—technique where two beams excite a material from opposite sites

2. Exemplary Embodiments

Although the following detailed description contains many specifics for the purposes of illustration, anyone of ordinary skill in the art will appreciate that many variations and alterations to the following details are within the scope of the invention. Accordingly, the following embodiments of the invention are set forth without any loss of generality to, and without imposing limitations upon, the claimed invention.

The present invention provides a novel methodology and applications that overcome limitations of conventional methods of using materials and light in marking technologies.

Figure 1:
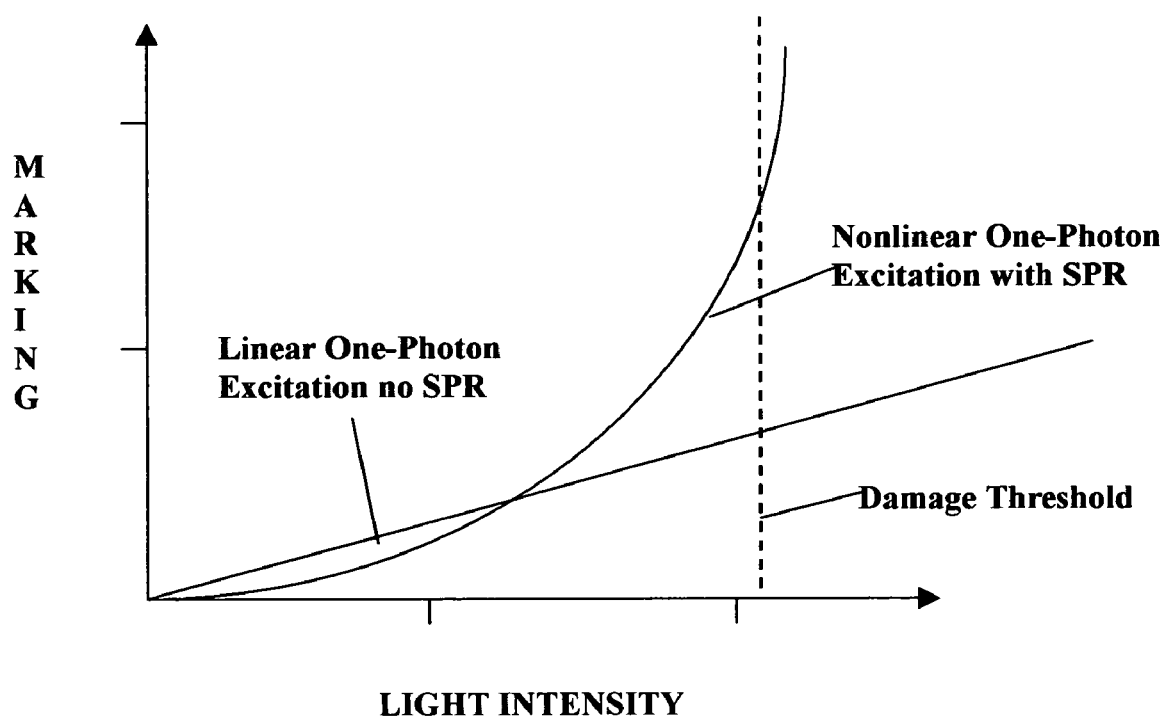
FIG. 1 shows linear and nonlinear marking dependence vs. the electromagnetic (EM) field strength (light intensity) for the chemical substance excited with one- and two-photon in the absence and presence of surface plasmon resonance (SPR) enhancement. It is clearly evident that nonlinear excitations with the SPR enhancement provide much better marking efficiency.

The present invention relates to a new method and new applications of surface plasmon resonance (SPR) enhanced interactions of nanoparticles with marking substances. The method utilizes the interactions to enhance absorption and fluorescence rates of the substances for marking purposes. The marking efficiency is significantly improved in the proposed method, which is truly needed in marking technologies. Additionally, the SPR-enhanced marking with one- and multi-photon excitation modes provide very sensitive and less destructive marking to a medium in which are embedded the nanoparticles and marking substances. FIG. 1 shows linear and nonlinear marking efficiency dependence vs. SPR intensity for the marking substance excited with one-photon in the absence and presence of the SPR enhancement. It is clearly evident that marking with the SPR enhancement provide better marking efficiency with less invasiveness to media in which are performed marking. In addition, by using wavelengths of light for the SPR-enhanced marking which are not absorbed by the media, the marking can be performed totally non-invasively to media. Therefore, the SPR-enhanced marking can be performed on very fragile materials, like plastic, thin foils or biomaterials.

Figure 2:
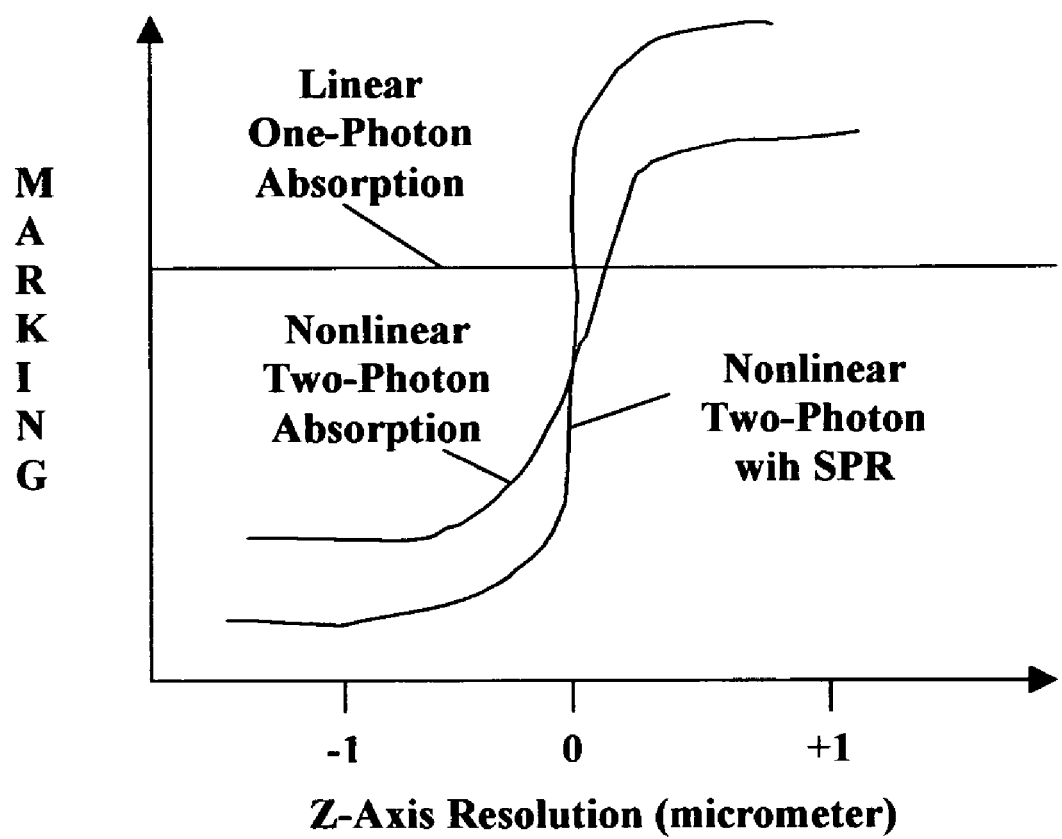
FIG. 2 shows the z-axis resolutions with one-photon and two-photon excitations in the absence of SPR, and with two-photon excitation in the presence of SPR.
Figure 3:
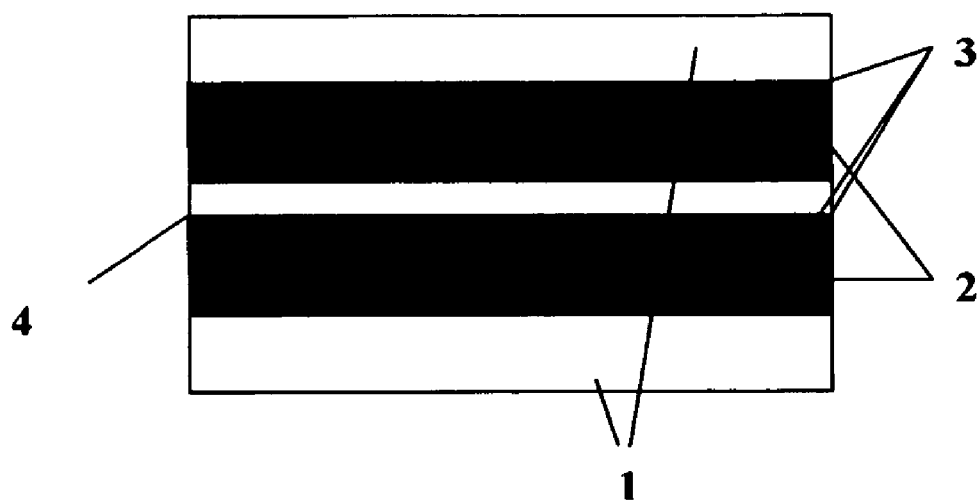
FIG. 3 shows a memory disk comprised of several layers: an optically transparent layer (1), several writing information layers (2) where each of them is attached to a chemical acceptor layer (3) and spacer (4), and another optically transparent layer (1).
Figure 4:
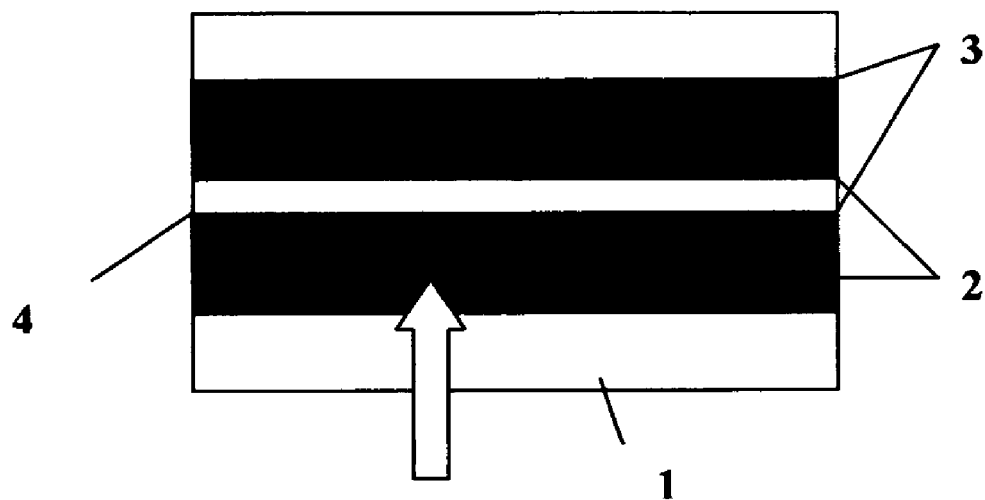
FIG. 4 shows an example of how information can be written on each different layer (2) by using a multiphoton microscopy technique with three-dimensional resolution that is obtained by simultaneous absorption of two or more photons. In that technique, the lateral writing resolution would be close to a value half that of the used wavelength, and the z-resolution would be twice higher than the used wavelength.
Figure 5:
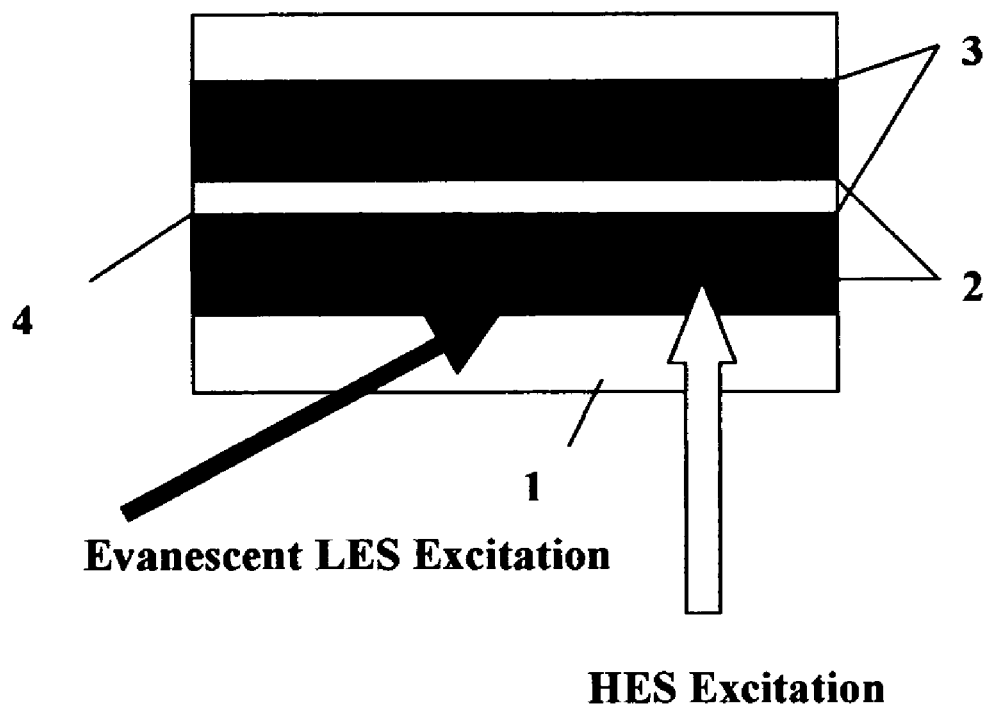
FIG. 5 shows an example of a method which applies exponential intensity decay of the evanescent light from the plasmon-activated surface to increase writing resolution in the z-direction. Under a specific angle of illumination, evanescent light excites chemical substances to LES in a very well-defined place in the writing layer (2) and at the same time, another light transparent to all layers excites the LES excited chemical substance to HES. This method leads to better than the diffraction limit writing resolution.

The method of SPR-enhanced marking with multiphoton and step-wise excitations also provides better three-dimensional resolutions than non-SPR assisted marking with multiphoton excitation and step-wise excitations (FIG. 2.). Better resolutions are related to higher optical nonlinearity of SPR-assisted marking. Resolution improvement in marking technology is needed for marking information on memory devices, CD disks, and DVD disks, but not limited to them. The SPR-enhanced marking can be performed in a one-photon excitation mode or in a two-photon mode or in an evanescent mode or in plurality photon excitation modes. In addition to these modes, marking can be performed with multiple wavelengths. An example of using this method for marking is shown in FIG. 3, where a memory disk comprised of several layers: a) an optically transparent layer (1), b) several writing information layers (2) where each of them is attached to a chemical acceptor layer (3) and spacer (4), c) another optically transparent layer (1). The writing layer is made of material which will ionize at specific light energies, and during the ionization process, one of the ionization products is accepted by the nearby chemical acceptor layer (3) and another product will remain in the writing layer (2). Such writing material, for example, can be made of a metal dioxide, and after the ionization of such metal dioxide, the metal remains in the writing layer and the chemical acceptor layer absorbs dioxide. The metal having different spectral properties than metal dioxide can be used as a marker for writing information. The presented SPR method of writing can be performed on an atomic/molecular level of resolution, which is much better than the diffraction limit of light. Two additional examples illustrating the writing of information on the disk are shown on FIG. 4 and FIG. 5. In the Example 1, information can be written on each different layer by using a multiphoton microscopy technique with three-dimensional resolution that is obtained by simultaneous absorption of two or more photons. In that technique, the lateral writing resolution would be close to a value half that of the used wavelength, and the z-resolution would be twice higher than the used wavelength. An increased spatial resolution in the z-direction with the use of the evanescent technique is presented in Example 2. The method uses exponential intensity decay of evanescent light from the plasmon-activated surface to increase writing resolution in the z-direction. Under a specific angle of illumination, evanescent light excites chemical substances to LES in a very well defined place in the writing layer and at the same time another light transparent to all layers excites the LES excited chemical substance to HES. This method leads to better than diffraction limit writing resolution. Any variations of excitation modes, e.g. evanescent, one-photon, multiphoton, step-wise, 4-Pi or others, in SPR-enhanced marking are considered as embodiments of this invention.

Figure 6:
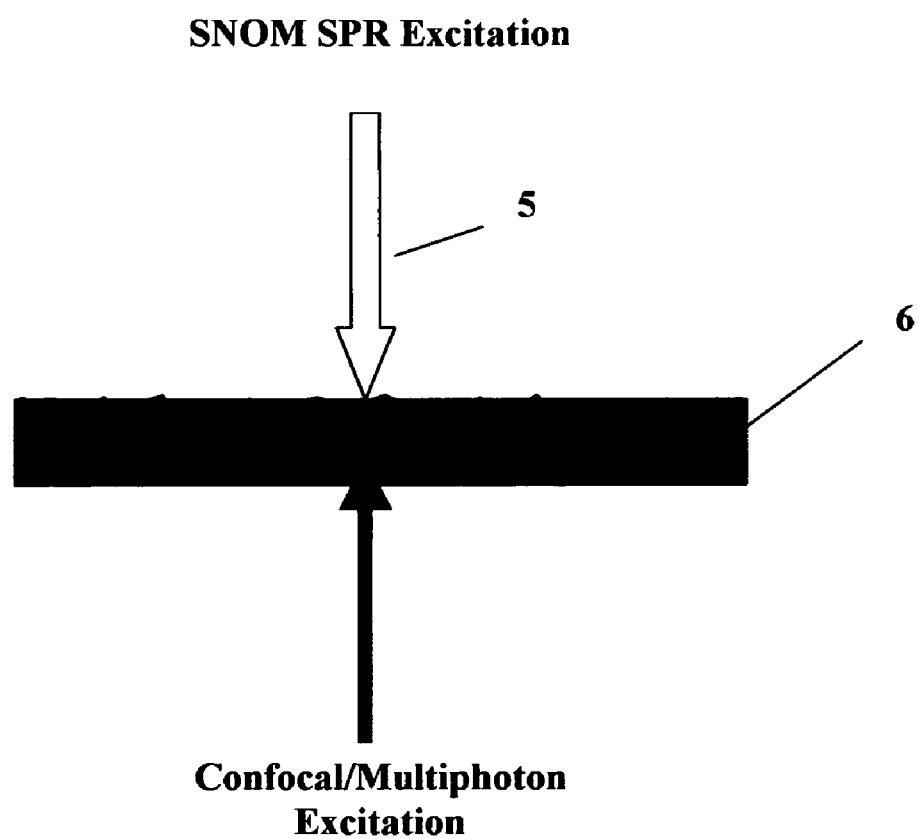
FIG. 6 shows a scanning near field optical microscope (SNOM) technique, in which a nanometer-sized metallic tip (5) under optical illumination generates SPR, which can be used for marking materials (6) with a subwavelength resolution. Adding marking volume controlled by confocal/multiphoton optical excitation may provide the method and instrument for two- and three-dimensional subwavelength SPR-enhanced marking. Such a marking technique can be performed on biomaterials as well as on recording materials and others. The technique can also be used to readout information from already marked material.

Another embodiment of the invention applies also to SPR-enhanced marking with a scanning near field optical microscope (SNOM) and/or confocal/multiphoton microscope techniques (FIG. 6.). In the SNOM technique, a nanometer-sized metallic tip (5) under optical illumination generates SPR, which can be used for marking of materials (6) with a subwavelength resolution. Adding marking volume controlled by confocal/multiphoton optical excitation may provide the method and instrument for two- and three-dimensional subwavelength SPR-enhanced marking. Such marking techniques can be performed on biomaterials and on recording materials and others. The instrument can also be used to readout information from already marked material.

Surface plasmon resonance-excited metal nanoparticles can also enhance the rate of transient absorption by excited molecules in a resonant two-photon higher excited states (HES) excitation (M. D. Galanin, and Z. A. Chizhikova, "Fluorescence from the second excited electronic level and absorption by excited R6G molecules", *Bull. Acad. Sc., Phys. Ser.* 36, 850 (1972)). The first photon excites the long-living lowest excited state (LES), and then the second photon populates the HES through the SPR-enhanced absorption. Such a step-wise two-photon HES excitation (M. D. Galanin, and Z. A. Chizhikova, "Fluorescence from the second excited electronic level and absorption by excited R6G molecules", *Bull. Acad. Sc., Phys. Ser.* 36, 850 (1972)) is then followed by the SPR-enhanced fluorescence. The resonance- and SPR-enhanced two-photon excitation will greatly increase the intensity of the SPR-enhanced HES absorption and/or emission. This is our concept behind the method of less invasive and very efficient SPR-enhanced marking.

Figure 7:
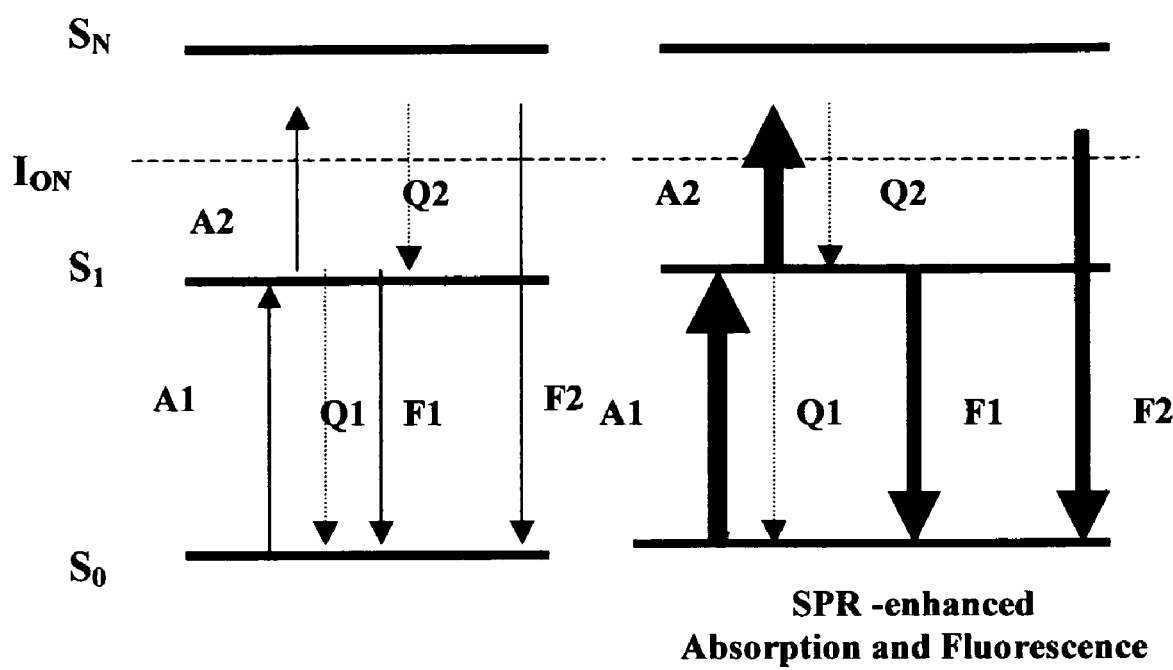
FIG. 7 shows Jablonski's electronic structure diagram of DNA in the absence and presence of SPR. The A1 and A2 absorption rates correspond to LES and HES absorption, respectively. The Q1 and Q2 quenching rates and F11 and F12 fluorescence rate correspond to LES and HES quenching and fluorescence, respectively. The absorption and fluorescence rates are a few orders of magnitude smaller than absorption and fluorescence rates in the presence of SPR, which is indicated by thicker arrows for transitions in the presence of SPR.
Figure 8:
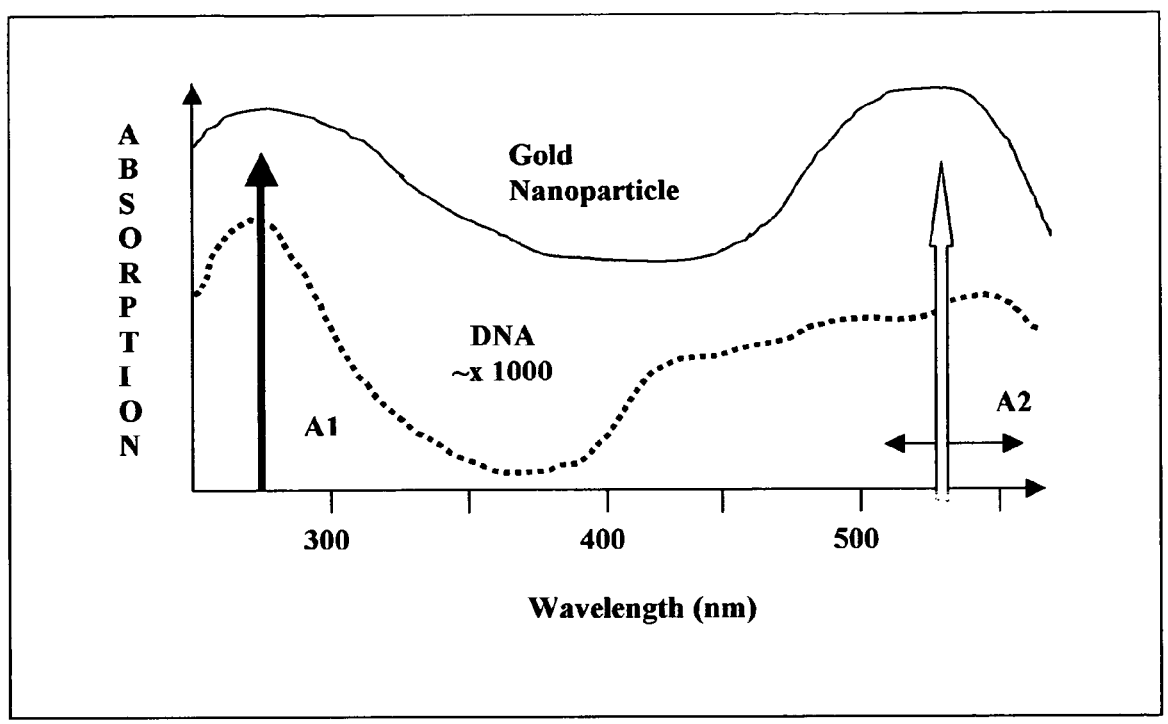
FIG. 8 shows step-wise absorption spectra of DNA and absorption bands of gold nanoparticles, respectively. The LES and HES absorption bands of DNA overlap with absorption bands of gold nanoparticles. The absorption coefficients of the both DNA bands are a few orders of magnitude smaller than the absorption bands of gold nanoparticles.

In one of the embodiments, the method of SPR-enhanced LES and HES absorption bands of biomaterials is applied for more efficient and minimally-invasive crosslinking of biomaterials. Current techniques for DNA-protein photocrosslinking predominantly use a UV pulse laser (Akhilesh K. Nagaich, Dawn A. Walker, Ron Wolford, and Gordon L. Hager, Rapid Periodic Binding and Displacement of the Glucocorticoid Receptor during Chromatin Remodeling, Molecular Cell, Vol. 14, 163-174(2004)) or a femtosecond two-wavelength laser (Ch. Russmann, J. Stollhof, C. Weiss, R. Beigang and M. Beato, Two wavelength femtosecond laser induced DNA-protein crosslinking, *Nucleic Acids Research,* Vol. 26, No. 17 3967-3970 (1998)). In the first technique, DNA absorption of two UV photons provides only a few percent of crosslinking efficiency and is associated with substantial DNA damage. The second femtosecond technique is less invasive to DNA and provides significantly higher crosslinking efficiency. However, both techniques require significant intensity of UV and/or VIS-NIR light for crosslinking because of very small DNA LES and HES absorption coefficients (Jean-Marc L. Pecourt, Jorge Peon, and Bern Kohler, Ultrafast Internal Conversion of Electronically Excited RNA and DNA Nucleosides in Water, *J. Am. Chem. Soc.* 122, 9348-9349 (2000)). The intense UV light generates unwanted two-photon photolysis of water and photodamage of DNA, proteins and other molecules. Very intense VIS-NIR light in the femtosecond two-wavelength technique may also disturb the crosslinking process in vivo applications, where VIS-NIR light is strongly absorbed by living bodies. The method described in the invention mitigates the above disadvantages of crosslinking techniques by significant enhancement of LES and HES absorption coefficients of biomolecules that are nearby SPR excited metal nanoparticles. The SPR-enhanced crosslinking leads to highly efficient, sensitive and minimally invasive biomaterials crosslinking. The method is illustrated in FIGS. 7 and 8, where illustrated is Jablonski's electronic structure diagram of DNA, step-wise absorption spectra of DNA and absorption bands of gold nanoparticles, respectively. The LES and HES absorption bands of DNA overlap with absorption bands of gold nanoparticles. The absorption coefficients of both DNA bands are a few orders of magnitude smaller than the absorption bands of gold nanoparticles. This means that under SPR nonlinear interactions of gold nanoparticles with nearby DNA, the absorption coefficients of DNA can be enhanced by a few orders of magnitude due to their EM dipole-dipole interactions and the nonlinear nature of these interactions. As a result, SPR-enhanced crosslinking can be performed with much less intense and less expensive light sources, such as compact lasers or lamps. The method applies in this embodiment to different modes of excitation, like step-wise one-wavelength, step-wise multiwavelength, two-photon one-wavelength, two-photon multiwavelength or direct one-photon wavelength. The presented DNA-protein crosslinking method is only one example of many other applications of this method. The method can be applied to tissue surgery, tattoo writing or removing, crosslinking biomaterials and other chemical substances. Another embodiment in this invention relates to applications of SPR-enhanced marking for drug delivery, photodynamic therapy, and other medical problems, but not limited to them. In many cases, drug delivery to the body is hindered by the low solubility of the drug in body fluids or body tissue. The low solubility of the drug can be related to the hydrophobic properties of the drug which leads to less effective treatment. To increase solubility of the drug, the SPR-enhanced marking method disclosed in this invention can be applied. Two of many examples of drug delivery assisted with SPR-enhanced marking are described here as follows. A drug chemically linked to a nanoparticle or nearby of the nanoparticle can be very efficiently excited by SPR of the nanoparticle. The excited drug can display a million-fold increased interaction with surrounding water molecules leading to better solubility of the drug. Another scenario of SPR-increased solubility of the drug can be that the nanoparticle linked to the drug will increase hydrophilicity under SPR, for example titanium dioxide nanoparticles under UV excitation will dissociate for a titanium metal nanoparticle and an oxygen molecule and SPR of the titanium nanoparticle will enhance hydrogen bonding of surrounding water with the oxygen molecules. One of many advantages of the SPR-increased solubility of drugs is that photodynamic therapy can be performed more effectively at specific locations in the body. However, there are some medical treatments in which high solubility of a drug can be problematic. In these cases, a drug can be embedded in a polymer-coated nanoparticle, and the nanoparticle can deliver the drug to specific locations in the body and under the SPR excitation, the drug can be released from the nanoparticles.

The method presented in the invention can be also applied to cosmetics and topical medicines for more effective skin treatment. The SPR-enhanced hydrophilic or hydrophobic properties of cosmetics can provide better cosmetic/dermatological treatment, such as better hydrated and moisturized skin conditions in the enhanced antibacterial environment.

Another embodiment in this invention uses the method of SPR-enhanced LES and HES absorption rates for more effective photodynamic therapy. The current photodynamic therapy techniques use protoporphyrin derivatives and light to induce photooxidation processes in cancer cells to damage these cells. The rate of these photooxidation processes can be increased a thousand fold in the presence of SPR. In addition, the SPR-enhanced crosslinking of biomaterials in cancer cells, particularly with the contribution of the SPR-enhanced HES absorption, can provide a very effective photodynamic therapy. The SPR excited nanoparticles can be also used themselves in photodynamic therapy. The very strong EM field surrounding nanoparticles and the SPR-enhanced redox properties of the nanoparticles may effectively interact with cancer cells causing their damage. This therapy can be even more effective with applying the SPR-enhanced two-wavelength excitations. One of the wavelengths can be matched with absorption of biomaterials in cancer cells and another wavelength can be matched with singlet oxygen generation and/or with heat production.

Anyone of ordinary skill in the art will appreciate the method of SPR-enhanced multiband fluorescence for marking and marking identification. A SPR-enhanced fluorescence intensity ratio of LES and HES depends mainly from a distance of SPR-excited nanoparticles to fluorophores. Therefore, by designing the distance, one can create a unique identification spectral key, which can be used as hidden information in valuable papers, ID cards, but not limited to them. The SPR-enhanced multiband fluorescence can be also used for a direct marking photosensitive medium and chemical substance or for fluorescence resonance energy transfer to chemical substance and/or medium. Because of much lower intensities of the SPR-enhanced fluorescence and different fluorescence emission wavelengths than the SPR excitation source, the SPR-enhanced fluorescence marking can be performed on extremely fragile materials.

Another embodiment in this invention uses SPR-enhanced marking to increase hydrophilicity, hydrophobicity, and antibacterial properties of the medium and/or the chemical substance. Increasing any of these properties is related to the SPR-excited nanoparticle and to the SPR-enhanced absorption rates of LES and HES of the medium and the chemical substance. Under such a thousand fold absorption enhancement, the medium, chemical substance and SPR-excited nanoparticle create enhanced hydrophilic, hydrophobic and antibacterial surrounding environment. The SPR-enhanced properties of the medium and/or the chemical substance can be designed for specific applications, such as in textile materials for water and dirt repellency with antibacterial properties, in sanitary units for easy cleaning and maintaining an antibacterial environment, in car windows and mirrors for maintaining antifogging and antibacterial conditions, in microarray assays in which induced hydrophilic spots in surrounding hydrophobic environments concentrate more analytes for detection, but not limited to these examples. The method allows for simultaneous contribution of both LES and HES of the medium and/or the chemical substance to increase these properties. For example, photocatalytic and antibacterial properties of titanium dioxide embedded to the medium would not require the use of only strong UV light. The VIS-NIR light can be used together with much weaker UV light to maintain these properties. Therefore, in the presence of SPR, the sunlight broad spectrum can very effectively contribute to LES and HES transitions. The medium is selected from the group of organic and inorganic substances, biomaterial, polymer, plastic, liquid, glass, textile material, and not limited to them. The chemical substance is selected from the group metal nanoparticle, organic substance, inorganic substance, composition of organic and inorganic substances, biological substance, drug, stain, fluorescence dye, light sensitive substance, light sensitive polymer, environmentally sensitive polymer, chemically active substance, but not limited to them.

What is claimed is:

1. A method for surface plasmon resonance enhanced marking of a medium selected from the group consisting of a solid-state material, a human body, an animal body, or plant comprising the steps of:
    providing a composition capable of marking the medium when the composition is irradiated by radiation from a plasmon source, the composition comprising a nanoparticle and a marking substance, wherein the marking substance is attached to the nanoparticle;
    embedding the composition into the medium; and
    irradiating the embedded composition by the plasmon source.

2. The method of claim 1, wherein said nanoparticle is made of a metal, metal oxide, metal dioxide, metallic salt, intermetallic alloy, transition metal, electric conductor, electric superconductor, electric semiconductor, electric semiconductor doped with metal, quantum dot, dielectric, alkaline earth metal, earth rare element, carbon nanotube, aerogel metal composition, or doped metal composition.

3. The method of claim 2, wherein said metal is selected from the group consisting of silver, ruthenium, platinum, palladium, cobalt, rhenium, rhodium, osmium, iridium, copper, aluminum, aluminum alloy, zinc, nickel, chromium, magnesium, tungsten, iron, palladium, gold, titanium, selenium, cadmium, vanadium, molybdenum.

4. The method of claim 1, wherein the nanoparticle has a size within a range of 0.1 nm to 500,000 nm in at least one of its dimensions.

5. The method of claim 4, wherein said nanoparticle is a thin film, colloid, fiber, nanoisland, nanowire, nanotube, empty shell, shell filled with a conducting material, shell filled with a dielectric material, or shell filled with a semiconductor material.

6. The method of claim 1, wherein the nanoparticle is a non-coated nanoparticle or the nanoparticle is a coated nanoparticle with at least one of the following coating substances: semiconductor, conductor, organic substance, biological substance, liquid crystal, inorganic substance, polymer, light sensitive polymer, environmentally sensitive polymer, recognitive material, biorecognitive material, chemical ligand, immunolabels, or phage display.

7. The method of claim 1, wherein the marking substance is selected from the group of: organic substance, inorganic substance, biological substance, drug, stain, or fluorescence dye.

8. The method of claim 7, wherein the biological substance is an oligonucleotide, DNA, RNA, protein, amino acid, lipid, peptide, or biomolecule.

9. The method of claim 1, wherein the nanoparticle is a single-type nanoparticle or a plurality of nanoparticles.

10. The method of claim 1, wherein the plasmon source is a single electromagnetic energy source or a multiple electromagnetic energy source.

11. The method of claim 10, wherein the electromagnetic energy source is selected from the group consisting of: a laser with single wavelength, laser with plurality wavelengths, semiconductor laser, pulsed laser, CW laser, Q-switched laser, light emitting diode, lamp, organic light emitting diode, X-Rays source, chemiluminescence source, fluorescence source, sun light source, or electroluminescence source.

12. The method of claim 11, wherein said electromagnetic energy source has a wavelength or wavelengths within a range of 0.001 nm to 200,000 nm.

13. The method of claim 1, wherein the plasmon source is irradiating the embedded composition in a one-photon mode, two-photon mode, multi-photon mode, two-wavelength two-photon mode, step-wise mode, up-conversion mode, harmonic generation mode, two-wavelength two-photon step-wise mode, evanescence mode, or plurality of optical excitation modes.

* * * * *